United States Patent
Kontiola et al.

(10) Patent No.: US 12,031,809 B2
(45) Date of Patent: Jul. 9, 2024

(54) SYSTEM AND METHOD FOR DETECTING A WAVE OCCURRING IN/ON A MEMBRANE

(71) Applicant: PHOTONO OY, Helsinki (FI)

(72) Inventors: Antti Kontiola, Helsinki (FI); Ari Salmi, Helsinki (FI); Risto Montonen, Helsinki (FI); Edward Haeggström, Helsinki (FI)

(73) Assignee: PHOTONO OY, Helsinki (FI)

( * ) Notice: Subject to any disclaimer, the term of this patent is extended or adjusted under 35 U.S.C. 154(b) by 526 days.

(21) Appl. No.: 17/430,046

(22) PCT Filed: Feb. 25, 2020

(86) PCT No.: PCT/FI2020/050069
§ 371 (c)(1),
(2) Date: Aug. 11, 2021

(87) PCT Pub. No.: WO2020/165495
PCT Pub. Date: Aug. 20, 2020

(65) Prior Publication Data
US 2022/0113125 A1   Apr. 14, 2022

(30) Foreign Application Priority Data
Feb. 12, 2019   (FI) .................... 20195098

(51) Int. Cl.
*G01B 11/06*   (2006.01)
*A61B 3/10*   (2006.01)
(Continued)

(52) U.S. Cl.
CPC .......... *G01B 11/06* (2013.01); *A61B 3/1005* (2013.01); *G01H 9/00* (2013.01); *A61B 3/165* (2013.01); *A61B 5/0095* (2013.01)

(58) Field of Classification Search
CPC .......... G01B 11/06; G01B 17/02; G01B 9/02; A61B 3/1005; A61B 3/165; A61B 5/0095; A61B 8/10; G01H 9/00
See application file for complete search history.

(56) References Cited

U.S. PATENT DOCUMENTS

| 2004/0193033 A1 | 9/2004 | Badehi et al. |
| 2005/0030473 A1 | 2/2005 | Fahrenkrug et al. |

(Continued)

FOREIGN PATENT DOCUMENTS

| CN | 107607051 A | 1/2018 |
| CN | 107664476 A | 2/2018 |

(Continued)

OTHER PUBLICATIONS

Office Action and Search Report issued in Chinese Patent Application No. 202080013516.3 dated Jan. 12, 2023.

(Continued)

*Primary Examiner* — James C. Jones
(74) *Attorney, Agent, or Firm* — NIXON & VANDERHYE

(57) ABSTRACT

A system for detecting a wave occurring in/on a membrane includes a source for directing an excitation signal obliquely to the membrane and a receiver for measuring interference between a first part of the excitation signal reflected off a front surface of the membrane and a second part of the excitation signal reflected off a rear surface of the membrane. The system includes a processing device for detecting the wave based on a change in the measured interference. The detection of the wave is based on changes caused by the wave in the optical length of a V-shaped part of a propagation path of the second part of the excitation signal, where the V-shaped part of the propagation path is inside the membrane.

20 Claims, 3 Drawing Sheets

(51) Int. Cl.
*G01H 9/00* (2006.01)
*A61B 3/16* (2006.01)
*A61B 5/00* (2006.01)

(56) References Cited

U.S. PATENT DOCUMENTS

| | | |
|---|---|---|
| 2006/0209631 A1 | 9/2006 | Melese et al. |
| 2016/0066786 A1* | 3/2016 | Kontiola .............. A61B 3/1005 |
| | | 600/398 |
| 2016/0374554 A1 | 12/2016 | Kontiola et al. |
| 2016/0374555 A1 | 12/2016 | Kontiola et al. |
| 2018/0193194 A1 | 7/2018 | Haeggström et al. |
| 2019/0017807 A1 | 1/2019 | Kondo et al. |

FOREIGN PATENT DOCUMENTS

| | | |
|---|---|---|
| CN | 109253700 A | 1/2019 |
| DE | 10 2008 008732 | 8/2009 |
| WO | 03/036225 | 5/2003 |
| WO | 2016/009334 | 1/2016 |

OTHER PUBLICATIONS

International Search Report for PCT/FI2020/050069 mailed Jun. 2, 2021, 4 pages.
Written Opinion of the ISA for PCT/FI2020/050069 mailed Jun. 2, 2021, 5 pages.

* cited by examiner

SYSTEM AND METHOD FOR DETECTING A WAVE OCCURRING IN/ON A MEMBRANE

CROSS-REFERENCE TO RELATED APPLICATIONS

This application is the U.S. national phase of International Application No. PCT/FI2020/050069 filed Feb. 5, 2020 which designated the U.S. and claims priority to FI Patent Application No. 20195098 filed Feb. 12, 2019, the entire contents of each of which are hereby incorporated by reference.

BACKGROUND OF THE INVENTION

Field of the Invention

The disclosure relates to a system for detecting a wave occurring in/on a membrane, for example in/on the cornea of an eye. Furthermore, the disclosure relates to a method for detecting a wave occurring in/on a membrane.

Description of the Related Art

In many cases, there is a need to detect a wave, such as e.g. a membrane wave or a Lamb wave, occurring in/on a membrane. The wave can be either a standing wave or a travelling wave. In this document the word "membrane" is not limited to substantially 2-dimensional structures whose thickness is extremely small, but the word "membrane" can mean any material layer, a sheet, a plate, or another structure whose thickness is significantly smaller than the other dimensions. Detection of a wave occurring in/on a membrane can be utilized for example in eye pressure measurements where an excitation such as e.g. an air impulse, an ultrasonic tone burst, a shock wave, or some other suitable excitation is used to deform a cornea and thereafter an estimate of the eye pressure is obtained based on a wave caused by the excitation in/on the cornea. A wave occurring in/on a membrane can be detected for example using interferometry where radiation is directed to the membrane under consideration and to a reference reflector. The wave causes changes in the optical length of a propagation path of the radiation reflected off a surface of the membrane. Thus, the wave causes changes in the interference between the radiation reflected off the reference reflector and the radiation reflected off the surface of the membrane.

Therefore, the wave can be detected based on the changes of the above-mentioned interference.

In many applications, the above-described interferometry-based method for detecting a wave occurring in/on a membrane is however not free from challenges. For example, in conjunction with eye pressure measurements, it can be challenging to keep the reference reflector sufficiently stationary with respect to an eye being measured so that unintentional changes in the position and/or orientation of the reference reflector with respect to the eye do not disturb the eye pressure measurement too much. Thus, there is a need for technical solutions for detecting a wave occurring in/on a membrane so that there is no need for a reference reflector or some other element that must be accurately stationary with respect to the membrane carrying the wave to be detected.

SUMMARY OF THE INVENTION

The following presents a simplified summary to provide basic understanding of some aspects of different invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying and non-limiting embodiments of the invention.

In this document, the word "geometric" when used as a prefix means a geometric concept that is not necessarily a part of any physical object. The geometric concept can be for example a geometric point, a straight or curved geometric line, a geometric plane, a non-planar geometric surface, a geometric space, or any other geometric entity that is zero, one, two, or three dimensional.

In accordance with the invention, there is provided a new system for detecting a wave occurring in/on a membrane, e.g. in/on the cornea of an eye. The membrane can be any material layer, a sheet, a plate, or another structure whose thickness is significantly smaller than the other dimensions. A system according to the invention comprises:
- a source for directing a signal to the membrane, and
- a receiver for measuring interference between a first part of the signal reflected off a front surface of the membrane and a second part of the signal reflected off a rear surface of the membrane, and
- a processing device for detecting the wave based on changes in the measured interference.

The source and the receiver are positioned obliquely with respect to each other so that the signal is directed obliquely to the membrane when the receiver receives the reflected first and second parts of the signal.

The detection of the wave occurring on the membrane is based on changes caused by the wave in the length of a V-shaped part of a propagation path of the above-mentioned second part of the signal, wherein the V-shaped part of the propagation path is inside the membrane. The way how the wave changes the length of the above-mentioned V-shaped part is explained later in this document with reference to figures.

As the detection of the wave is based on the interference between the first part of the signal reflected off the front surface of the membrane and the second part of the signal reflected off the rear surface of the membrane, there is no need for a reference reflector and/or another element that must be accurately stationary with respect to the membrane carrying the wave to be detected.

In accordance with the invention, there is provided also a new method for detecting a wave occurring in/on a membrane, e.g. in/on the cornea of an eye. A method according to the invention comprises:
- directing a signal obliquely to the membrane, and
- measuring interference between a first part of the signal reflected off a front surface of the membrane and a second part of the signal reflected off a rear surface of the membrane, and
- detecting the wave based on a change in the measured interference.

Various exemplifying and non-limiting embodiments are disclosed and claimed.

Exemplifying and non-limiting embodiments both as to constructions and to methods of operation, together with additional objects and advantages thereof, are best understood from the following description of specific exemplifying embodiments when read in conjunction with the accompanying drawings.

The verbs "to comprise" and "to include" are used in this document as open limitations that neither exclude nor require the existence of un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF THE DRAWINGS

Exemplifying and non-limiting embodiments of the invention and their advantages are explained in greater detail below with reference to the accompanying drawings, in which.

DESCRIPTION OF THE PREFERRED EMBODIMENTS

The specific examples provided in the description below should not be construed as limiting the scope and/or the applicability of the accompanied claims. Lists and groups of examples provided in the description below are not exhaustive unless otherwise explicitly stated.

Figure 1A:
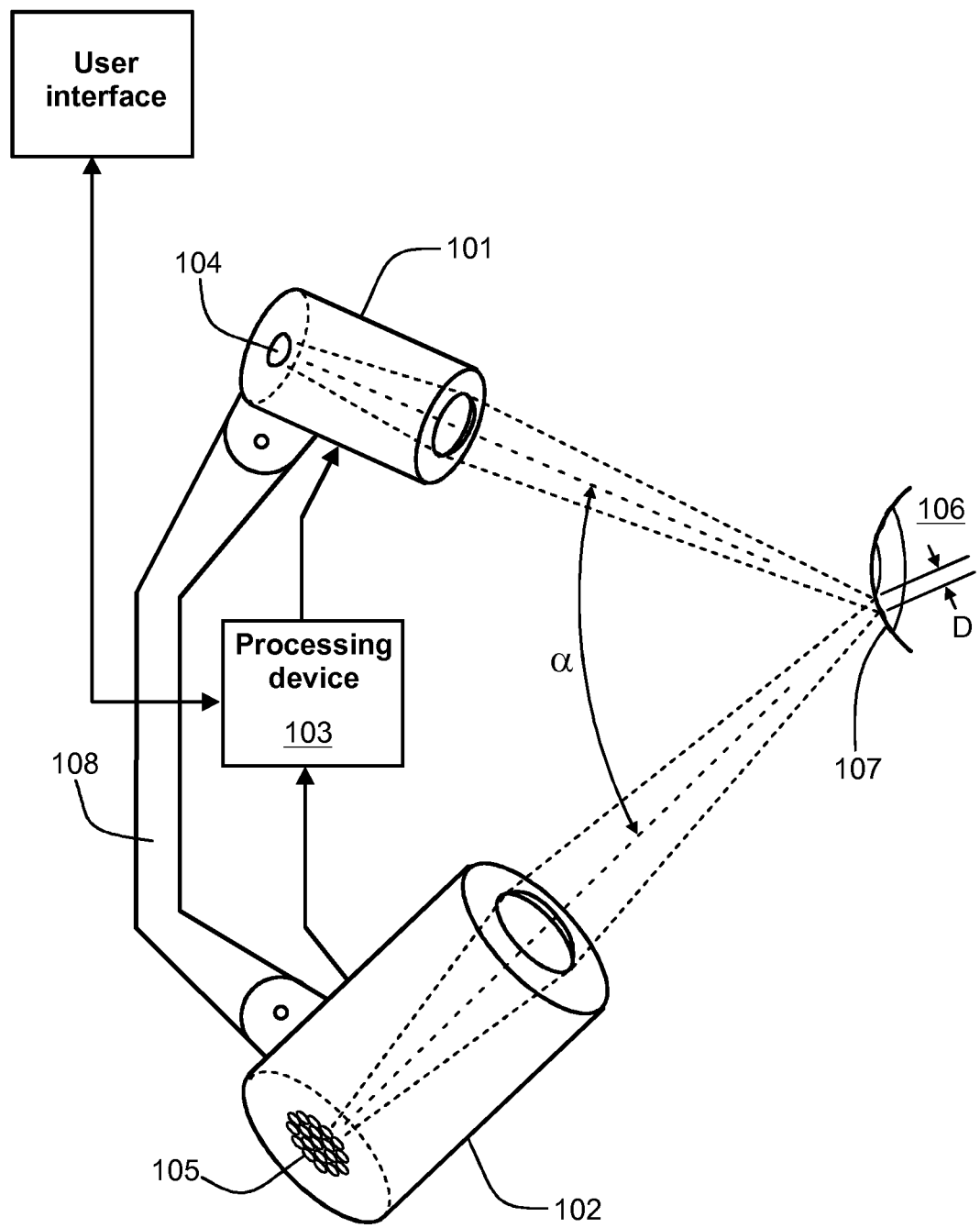
FIG. 1a illustrates a system according to an exemplifying and non-limiting embodiment for detecting a wave occurring in/on a membrane.
Figure 1B:
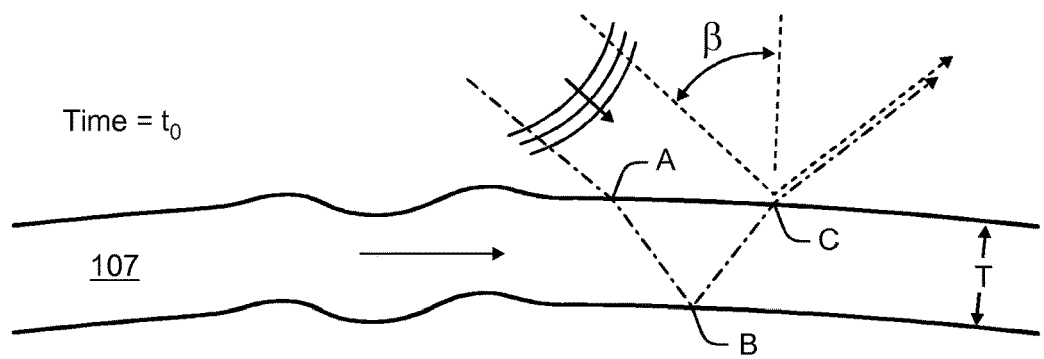
FIGS. 1b-1d illustrate the operational principle of the system illustrated in FIG. 1a, and FIG. 2 shows a flowchart of a method according to an exemplifying and non-limiting embodiment for detecting a wave occurring in/on a membrane.
Figure 1C:
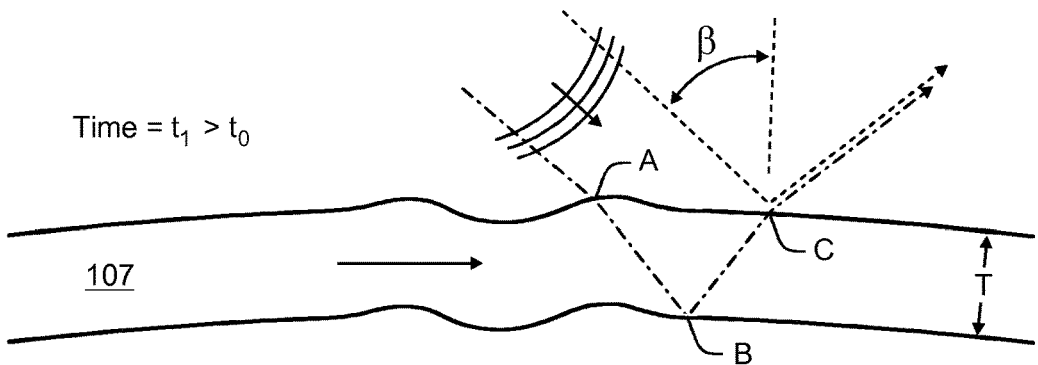
Figure 1D:
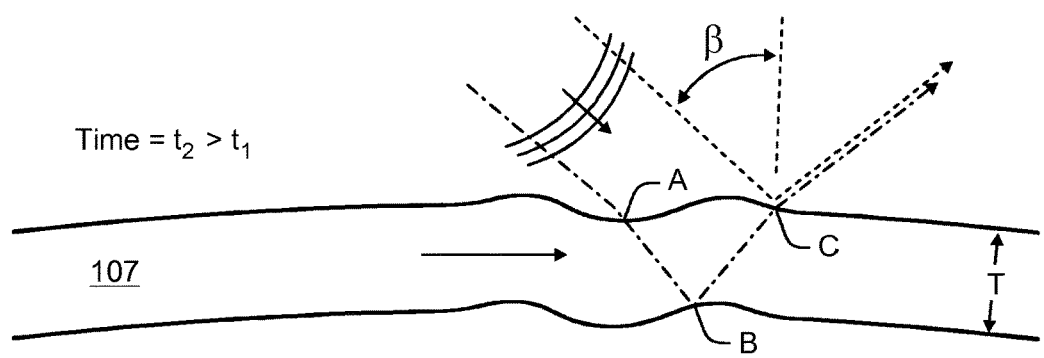

FIG. 1a illustrates a system according to an exemplifying and non-limiting embodiment for detecting a wave occurring in/on a membrane 107. In the exemplifying situation shown in FIG. 1a, the membrane 107 is the cornea of an eye 106. The wave that travels along the membrane 107 is illustrated in FIGS. 1b, 1c, and 1d which show a section view of the membrane 107 at different moments of time $t_0$, $t_1$, and $t_2$, where $t_2 > t_1 > t_0$. The system illustrated in FIG. 1a comprises a source 101 for directing a signal to the membrane 107. The source 101 may comprise for example a light source 104 that can be for example a laser source such as e.g. a vertical-cavity surface-emitting laser "VCSEL" for emitting the signal. In this exemplifying case, the signal is a light beam e.g. a laser beam. The source 101 may further comprise a lens system for focusing the light beam to the membrane 107. The light beam is advantageously focused on a front surface of the membrane 107 or behind the front surface. The front surface is the surface of the membrane 107 at which the signal arrives first. A diameter of a radiation spot, e.g. a laser spot, on the surface of the membrane 107 can be e.g. in the range from 0.5 mm to 6 mm. It is also possible that the signal is some other propagating wave-front e.g. an ultrasound wave-front. The system comprises a receiver 102 for measuring interference between a first part of the signal reflected off the front surface of the membrane 107 and a second part of the signal reflected off a rear surface of the membrane 107. In FIGS. 1b-1d, the first part of the signal is depicted with a dashed line arrow and the second part of the signal is depicted with a dash-and-dot line arrow. In exemplifying cases where the signal is electromagnetic radiation e.g. a laser beam, the receiver 102 may comprise for example a lens system and a multipoint sensor comprising an array of sensor elements 105. Each sensor element can be for example a photo-diode or a photo-transistor. It is also possible that the receiver 102 comprises a charge-coupled device "CCD". The system further comprises a processing device 103 for detecting the wave based on changes in the interference measured by the receiver 102. In a system according to an exemplifying and non-limiting embodiment, the receiver 102 comprises a dual photodiode or a photodiode array, where the differential sensing of the adjacent photodiodes is used to improve sensitivity.

The source 101 and the receiver 102 are positioned obliquely with respect to each other so that the signal is directed obliquely to the membrane 107 when the receiver 102 receives the reflected first and second parts of the signal. In a system according to an exemplifying and non-limiting embodiment, the source 101 and the receiver 102 are positioned obliquely with respect to each other so that an angle α between a transmission direction of the source 101 and a reception direction of the receiver 102 is in the range from 15 degrees to 120 degrees. In a system according to an exemplifying and non-limiting embodiment, the angle α is in the range from 45 degrees to 90 degrees.

The detection of the wave is explained below with reference to FIGS. 1b-1d. In the situation shown in FIG. 1b, the wave has not yet arrived at the radiated area of the membrane 107. The interference between the first and second parts of the signal is determined by the wavelength of the signal and the length of a V-shaped part A-B-C of the propagation path of the second part of the signal. In exemplifying cases where the signal is electromagnetic radiation e.g. a laser beam, it is assumed that the term "length" includes the effect of the refraction index of the material of the membrane 107. As shown by FIGS. 1b-1d, the V-shaped part of the propagation path is inside the membrane 107. In the situation shown in FIG. 1c, the wave has arrived at the excited area of the membrane 107. As illustrated in FIGS. 1b and 1c, the distance A-B is longer in the situation shown in FIG. 1c than in the situation shown in FIG. 1b and the distance B-C is substantially the same in the situations shown in FIGS. 1b and 1c. In the situation shown in FIG. 1d, the wave has moved further in the direction of propagation than in the situation shown in FIG. 1c. As illustrated in FIGS. 1d-1d, the distances A-B and B-C are shorter in the situation shown in FIG. 1d than in the situations shown in FIGS. 1b and 1c. The above-described variation in the length of the V-shaped part A-B-C of the propagation path of the second part of the signal causes changes in the interference between the first and second parts of the signal. As illustrated by FIGS. 1b-1d, the variation in the length of the V-shaped part A-B-C is strongest when a distance between the point A where the second part of the signal enters the membrane 107 and the point C where the second part of the signal exits the membrane 107 is substantially the length of the wave occurring in/on the membrane.

A system according to an exemplifying and non-limiting embodiment comprises a support structure 108 arranged to mechanically support the source 101 and the receiver 102 so that the above-mentioned angle α shown in FIG. 1a is changeable. This enables a user of the system to select the angle α so that the distance between the point A where the second part of the signal enters the membrane 107 and the point C where the second part of the signal exits the membrane 107 is substantially the length of the wave occurring in/on the membrane.

In a system according to an exemplifying and non-limiting embodiment, the processing device 103 is configured to estimate variation rate of the measured interference. The variation rate can be expressed e.g. in Hz. In some exemplifying cases, the variation rate can be for example above 1 kHz.

In a system according to an exemplifying and non-limiting embodiment, the processing device 103 is configured to estimate travelling speed of the wave based on the variation rate of the measured interference and pre-stored data indicative of the length of the wave. It is also possible that there are two measurement spots simultaneously on the membrane a known distance apart from each other, and the travelling speed is estimated based on the known distance and a time difference between respective changes taking place in the interferences measured for the two measurement spots.

In a system according to an exemplifying and non-limiting embodiment, the processing device 103 is configured to control the source 101 to vary the wavelength of the signal and to estimate the thickness of the membrane 107 based on the interference measured with different wavelengths of the signal. The thickness is denoted with T in FIGS. 1b-1d. In this exemplifying case, the source 101 may comprise for example a vertical-cavity surface-emitting laser "VCSEL" for implementing a wavelength sweep of the signal. The wavelength of the signal emitted by a VCSEL can be changed by changing electric current of the VCSEL. Thus, a VCSEL can be driven with ramped pulses of electric current in direct intensity modulation, and the intrinsic property of the VCSEL produces a wavelength-swept output through the self-heating effect. The signal emitted by a VCSEL has a long coherence length which makes it possible to measure thicknesses of membranes whose thicknesses are few millimeters, whereas a wavelength scan obtained by changing electric current of the VCSEL makes it possible to detect white light interference for coherence widths of few hundreds of micrometers. The system may comprise an airgap for acting as a reference for the thickness determination. Data indicative of the thickness being determined can be obtained with the aid of Fourier transformation of the measured interference signal. As the measurement is carried out not perpendicularly but obliquely, the effect of the obliqueness i.e. a cosine-error is advantageously compensated for in the thickness estimation. For another example, the thickness estimation can be based on for example a pre-stored reference model obtained with experiments carried out with reference membranes having predetermined thicknesses, where the reference model is indicative of the behavior of the interference as a function of the wavelength of the signal and as a function of the thickness of the membrane, i.e. the interference=f($\lambda$, T), $\lambda$ being the wavelength of the signal and T being the thickness of the membrane. The reference model can be implemented with e.g. a two-dimensional lookup table. The effect of the refraction index of the material of the membrane can be included in the reference model. The thickness of the membrane can be estimated by finding a value for the thickness in the reference model so that the behavior of the interference indicated by the reference model as a function of the wavelength is as close as possible to the behavior of the measured interference as a function of the wavelength. It is also possible that the thickness of the membrane is estimated with a mathematical model based on the theory of wave optics. The mathematical model gives the thickness estimate when parameters indicative of the behavior of the measured interference as a function of the wavelength are given as input data.

The processing device 103 can be implemented with one or more processor circuits, each of which can be a programmable processor circuit provided with appropriate software, a dedicated hardware processor such as for example an application specific integrated circuit "ASIC", or a configurable hardware processor such as for example a field programmable gate array "FPGA". Furthermore, the processing device 103 may comprise one or more memory circuits each of which can be for example a random-access-memory "RAM" circuit.

Figure 2:
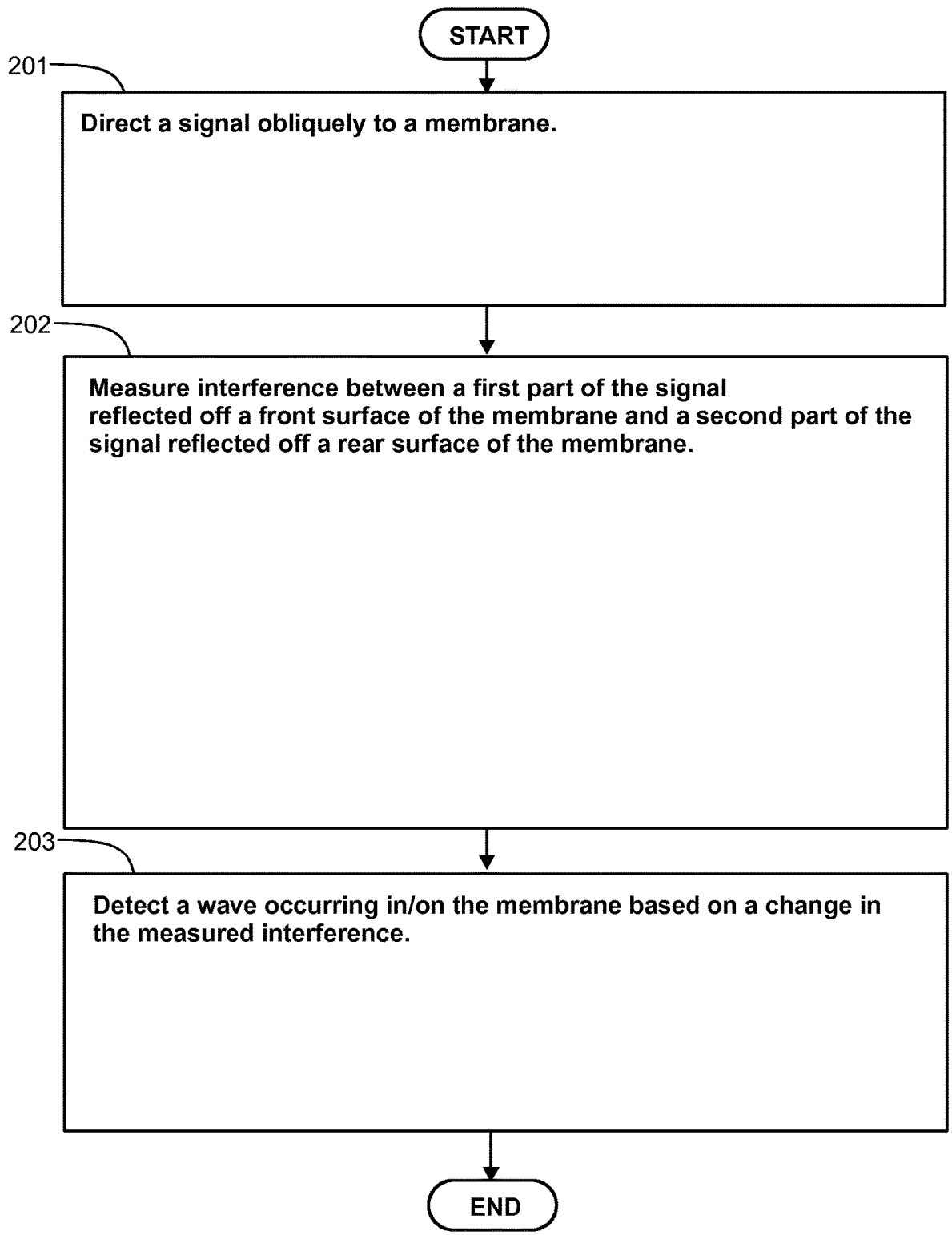

FIG. 2 shows a flowchart of a method according to an exemplifying and non-limiting embodiment for detecting a wave occurring in/on a membrane. The method comprises the following actions:
- action 201: directing a signal obliquely to the membrane, and
- action 202: measuring interference between a first part of the signal reflected off a front surface of the membrane and a second part of the signal reflected off a rear surface of the membrane, and
- action 203: detecting the wave based on a change in the measured interference.

In a method according to an exemplifying and non-limiting embodiment, the signal is directed obliquely to the membrane so that an angle $\beta$ between the arrival direction of the signal at the membrane and a geometric perpendicular of the membrane is in the range from 7 degrees to 60 degrees. The angle $\beta$ is illustrated in FIGS. 1b-1d. In a method according to an exemplifying and non-limiting embodiment, the above-mentioned angle $\beta$ is in the range from 22 degrees to 45 degrees.

In a method according to an exemplifying and non-limiting embodiment, the above-mentioned angle $\beta$ is selected so that a distance between a point where the second part of the signal enters the membrane and another point where the second part of the signal exits the membrane is substantially the length of the wave.

A method according to an exemplifying and non-limiting embodiment comprises estimating variation rate of the measured interference.

A method according to an exemplifying and non-limiting embodiment comprises estimating travelling speed of the wave based on the variation rate of the measured interference and pre-stored data indicative of the length of the wave.

A method according to an exemplifying and non-limiting embodiment comprises varying a wavelength of the signal and estimating the thickness of the membrane based on the measured interference corresponding to different wavelengths of the signal.

In a method according to an exemplifying and non-limiting embodiment, the signal is produced with a laser source, e.g. a vertical-cavity surface-emitting laser.

In a method according to an exemplifying and non-limiting embodiment, the interference is measured with an array of sensor elements.

The non-limiting, specific examples provided in the description given above should not be construed as limiting the scope and/or the applicability of the appended claims. Furthermore, any list or group of examples presented in this document is not exhaustive unless otherwise explicitly stated.

What is claimed is:

1. A system for detecting a wave occurring in/on a membrane, the system comprising:
   a source for directing a signal to the membrane, and
   a receiver for measuring interference between a first part of the signal reflected off a front surface of the membrane and a second part of the signal reflected off a rear surface of the membrane,
wherein the source and the receiver are positioned obliquely with respect to each other so that the signal is directed obliquely to the membrane when the receiver receives the reflected first and second parts of the signal, and the system comprises a processing device for detecting the wave based on a change in the measured interference.

2. The system according to claim 1, wherein the source and the receiver are positioned obliquely with respect to each other so that an angle between a transmission direction of the source and a reception direction of the receiver is in a range from 15 degrees to 120 degrees.

3. The system according to claim 2, wherein the source and the receiver are positioned obliquely with respect to each other so that the angle is in a range from 45 degrees to 90 degrees.

4. The system according to claim 1, wherein the system comprises a support structure arranged to mechanically support the source and the receiver so that an angle between a transmission direction of the source and a reception direction of the receiver is changeable.

5. The system according to claim 1, wherein the processing device is configured to control the source to vary a wavelength of the signal and to estimate a thickness of the membrane based on the interference measured with different wavelengths of the signal.

6. The system according to claim 1, wherein the source comprises a laser source.

7. The system according to claim 6, wherein the laser source is a vertical-cavity surface-emitting laser.

8. The system according to claim 1, wherein the receiver comprises an array of sensor elements.

9. A method for detecting a wave occurring in/on a membrane, the method comprising:
    directing a signal to the membrane, and
    measuring interference between a first part of the signal reflected off a front surface of the membrane and a second part of the signal reflected off a rear surface of the membrane,
wherein the signal is directed obliquely to the membrane, and the method comprises detecting the wave based on a change in the measured interference.

10. The method according to claim 9, wherein the signal is directed obliquely to the membrane so that an angle between an arrival direction of the signal at the membrane and a geometric perpendicular of the membrane is in a range from 7 degrees to 60 degrees.

11. The method according to claim 10, wherein the angle is in a range from 22 degrees to 45 degrees.

12. The method according to claim 9, wherein the method comprises selecting an angle between an arrival direction of the signal at the membrane and a geometric perpendicular of the membrane so that a distance between a point where the second part of the signal enters the membrane and another point where the second part of the signal exits the membrane is substantially a length of the wave.

13. The method according to claim 9, wherein the method comprises varying a wavelength of the signal and estimating a thickness of the membrane based on the measured interference corresponding to different wavelengths of the signal.

14. The method according to claim 9, wherein the signal is produced with a laser source.

15. The method according to claim 9, wherein the interference is measured with an array of sensor elements.

16. The system according to claim 2, wherein the system comprises a support structure arranged to mechanically support the source and the receiver so that an angle between a transmission direction of the source and a reception direction of the receiver is changeable.

17. The system according to claim 3, wherein the system comprises a support structure arranged to mechanically support the source and the receiver so that an angle between a transmission direction of the source and a reception direction of the receiver is changeable.

18. The system according to claim 2, wherein the processing device is configured to control the source to vary a wavelength of the signal and to estimate a thickness of the membrane based on the interference measured with different wavelengths of the signal.

19. The system according to claim 3, wherein the processing device is configured to control the source to vary a wavelength of the signal and to estimate a thickness of the membrane based on the interference measured with different wavelengths of the signal.

20. The system according to claim 4, wherein the processing device is configured to control the source to vary a wavelength of the signal and to estimate a thickness of the membrane based on the interference measured with different wavelengths of the signal.

* * * * *